United States Patent [19]

Sakamoto

[11] Patent Number: 5,565,170

[45] Date of Patent: *Oct. 15, 1996

[54] MULTILAYER ANALYTICAL ELEMENT FOR ASSAYING FRUCTOSAMINE

[75] Inventor: Hisashi Sakamoto, Kyoto, Japan

[73] Assignee: Kyoto Daiichi Kagaku Co., Ltd., Kyoto-fu, Japan

[*] Notice: The term of this patent shall not extend beyond the expiration date of Pat. No. 5,366,868.

[21] Appl. No.: 417,849

[22] Filed: Apr. 6, 1995

Related U.S. Application Data

[63] Continuation of Ser. No. 88,356, Jul. 9, 1993, abandoned, which is a continuation-in-part of Ser. No. 753,371, Aug. 30, 1991, Pat. No. 5,366,868.

[30] Foreign Application Priority Data

Aug. 30, 1990 [JP] Japan ................................ 2-230912

[51] Int. Cl.$^6$ ............................................. G01N 33/48
[52] U.S. Cl. .......................... 422/56; 436/87; 436/170; 435/805
[58] Field of Search .................... 435/10, 25, 805; 436/87, 170; 422/56

[56] References Cited

U.S. PATENT DOCUMENTS

| | | |
|---|---|---|
| 4,642,295 | 2/1987 | Baker . |
| 4,645,742 | 2/1987 | Baker . |
| 4,956,301 | 9/1990 | Ismail et al. ............................ 436/87 |
| 5,055,388 | 10/1991 | Vogt et al. ............................ 435/10 X |

FOREIGN PATENT DOCUMENTS

| | | |
|---|---|---|
| 0085263 | 5/1983 | European Pat. Off. . |
| 0215170 | 3/1987 | European Pat. Off. . |
| 0250991 | 1/1988 | European Pat. Off. . |
| 0291060 | 4/1988 | European Pat. Off. . |
| 63-15168 | 1/1988 | Japan . |
| 63-304999 | 6/1988 | Japan . |
| 63-182567 | 7/1988 | Japan . |
| 113062 | 1/1989 | Japan . |

OTHER PUBLICATIONS

"Fructosamine: a new approach to the estimation of serum glycosylprotein. An index of diabetic control", Roger N. Johnson, Patricia A. Metcalf and John R. Baker, Clinica Chimica Acta 127, pp. 87–95 (1982).
World Patents Index Latest, Week 8822, Derwent Publications Ltd., London, GB' AN 88–152614 & JP–A–63 (Fuji Photo Film KK) 26 Apr. 1988 (abstract).

*Primary Examiner*—Lyle A. Alexander
*Attorney, Agent, or Firm*—Birch, Stewart, Kolasch & Birch, LLP

[57] ABSTRACT

A multilayer analytical element for assaying fructosamine having a liquid-impermeable support, a dried buffer-containing layer which contains a buffer having pH of 8 to 12 formed on the support, and a tetrazolium salt-containing layer which is laminated on the buffer-containing layer, which element assays fructosamine in a short time with good accuracy.

16 Claims, 3 Drawing Sheets ic element for measuring fructosamine in a sample
MULTILAYER ANALYTICAL ELEMENT FOR ASSAYING FRUCTOSAMINE This application is a continuation of application Ser. No. 08/088,356 filed on Jul. 9, 1993, now abandoned; which is a continuation-in-part of application Ser. No. 07/753,371 filed on Aug. 30, 1991, now U.S. Pat. No. 5,366,868.

BACKGROUND OF THE INVENTION

1. Field of the Invention

The present invention relates to a multilayer analytical element for assaying fructosamine in a body fluid, in particular, serum.

2. Description of the Related Art

For the measurement of fructosamine in serum, Johnson and Baker proposed a method comprising measuring the reducing power of fructosamine with Nitrotetrazolium Blue (NTB) under alkaline conditions (see Clinica Chimica Acta, 127 (1982) 87–95, Japanese Patent Publication No. 13062/1989, EP-A-085 263 and U.S. Pat. Nos. 4,642,295 and 4,645,742). In this method, the serum is preincubated for 10 minutes to remove the influence of reducing substances in the serum other than fructosamine by reacting such reducing substances with NTB to decompose them, and then the amount of NTB consumed in the following 5 minute period (namely from 10 minutes to 15 minutes) is measured since the amount of NTB which is consumed in this 5 minute period is proportional to the amount of fructosamine in the serum.

Japanese Patent Kokai Publication No. 182567/1988 and EP-A-215 170 disclose an end point assay in which interfering substances present in a sample are removed by treating them with a strong base, an oxidizing agent, or an enzyme, or by desalting, the pH of the sample is adjusted to a range between 10 and 14, a color reagent (a tetrazolium salt) is added, and the developed color is measured.

Japanese Patent Kokai Publication No. 15168/1988 and EP-A-250 991 disclose a method comprising pretreating a sample at neutral pH to remove reducing substances and/or turbid materials, adjusting the pH to a range between 10 and 12, and adding a color reagent.

Japanese Patent Kokai Publication No. 304999/1988 and EP-A-291 060 disclose a method comprising adding a buffer solution having a pH of 9 to 12, a color reagent, uricase and at least one detergent (surfactant) and, after 5 minutes at the earliest, chemically kinetically measuring the change in absorbance with time in the temperature range between 20° C. and 40° C.

The method of Johnson and Baker is a so-called wet chemistry method, and adjusts the temperature at 37° C. under alkaline conditions and then measures the change of absorbance in a time range between 10 minutes and 15 minutes.

The method of Japanese Patent Kokai Publication No. 182567/1988 and EP-A-215 170 is a two-step method, which is troublesome and time-consuming.

In the method of Japanese Patent Kokai Publication No. 304999/1988 and EP-A-291 060, the preincubation requires at least 5 minutes before the reducing substances are removed and turbidity is clarified.

In addition, all the above prior art methods involve wet chemistry, and measure the change of absorbance using a reaction cell.

In general, formazan, which is generated by reduction of a tetrazolium salt to be used in a color developing reaction with fructosamine, firmly sticks to the reaction cell or the flow cell and increases the background, which is a source of error. When fructosamine is measured with an automatic analyzer which is widely used in many facilities, generated formazan deposits in the reaction tube, the transportation tube, or the flow cell contaminate the automatic analyzer, so that other components cannot be measured. Since it is difficult to remove deposited formazan, various devices or parts should be immersed in a strong acid or a surfactant overnight.

A reagent for measuring fructosamine is a strong alkaline reagent, for example, having a pH of 10 or greater, and its waste liquid is strongly alkaline and pollutes the environment.

In contrast to the wet chemistry method, a so-called dry chemistry method is known. In the dry chemistry method, since one drop (several μl) of the sample is used for the reaction, the sample is dried when the reaction continues more than 10 minutes and accuracy in measurement deteriorates. When the measuring time is shortened to 10 minutes or less, the measurement is influenced by the reducing substances in the body fluid, so that accurate data are not obtained.

SUMMARY OF THE INVENTION

One object of the present invention is to provide an analytical element for measuring fructosamine in a sample of body fluid by a dry chemistry technique.

Another object of the present invention is to provide an analytical element for easily measuring fructosamine in a sample of body fluid in a short measuring time.

According to the present invention, there is provided a multilayer analytical element for assaying fructosamine consisting essentially of a liquid-impermeable support, a dried buffer-containing layer which contains a buffer having a pH of 8 to 12 formed on said support and a tetrazolium salt-containing layer which is independently prepared, dried and laminated on said buffer-containing layer.

DETAILED DESCRIPTION OF THE INVENTION

Figure 1A:
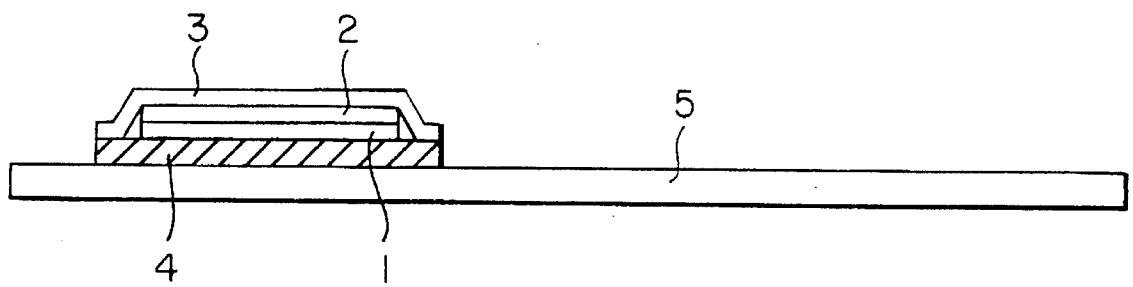
FIGS. 1A and 1B, 2A and 2B and 3A and 3B are cross-sectional views of the analytical elements produced in Examples 1 and 2 and the Comparative Example, respectively.

The liquid-impermeable support used in the present invention may be made of any liquid-impermeable material such as a plastic film, paper or a metal foil. Among them, the plastic film is preferred.

The buffer may be any one of conventional buffers having a buffering capacity in the pH range between 8 and 12, preferably between 8.5 and 10.5. In particular, a carbonate buffer is preferred.

The tetrazolium salt to be used in the present invention may be any one of conventional tetrazolium salts that will react with fructosamine to develop a color. Specific examples of the tetrazolium salt are:

3,3'-[3,3'-dimethoxy-(1,1'-biphenyl)-4,4'-diyl]bis [2-(p-nitrophenyl)-5-phenyl-2H-tetrazolium chloride](NTB), 3,3'-[3,3'-dimethoxy-(1,1'-biphenyl)-4,4'-diyl]bis [2,5-bis(p-nitrophenyl)-2H-tetrazolium chloride] (TNTB), 3,3'-(1,1'-biphneyl-4,4'-diyl)-bis(2,5-diphenyl-2H-tetrazolium chloride] (NeoTB), 3-(p-iodophenyl)-2-(p-nitrophenyl)-5-phenyl-2H-tetrazolium chloride (INT), 3-(4,5-dimethyl-2-thiazolyl)-2,5-diphenyl-2H-tetrazolium bromide (MTT), and 2,5-diphenyl-3-(1-naphthyl)-2H-tetrazolium chloride (TV).

The buffer-containing layer of the multilayer analytical element of the present invention may contain uricase. Since uricase decomposes uric acid, which is one of the reducing substances in body liquids, in a short time, it will suppress the influence of uric acid during the assay of fructosamine and shorten the assay time.

The multilayer analytical element of the present invention can be prepared by successively laminating the buffer-containing layer and the tetrazolium salt-containing layer on the liquid-impermeable support.

For example, the alkaline buffer-containing layer is formed on the support by dissolving the buffer and a binder in a suitable solvent, applying the resulting solution on the support, and drying it. Preferably, the binder is a hydrophilic polymer such as polyvinylpyrrolidone (PVP), hydroxypropylcellulose (HPC), methylcellulose (MC), polyacrylamide, gelatin, etc. When a hydrophilic polymer is used, the solvent is an aqueous solvent, in particular, water.

The tetrazolium salt-containing layer is formed by impregnating a solution of the salt in a porous matrix such as a filter paper, woven or knit fabric or a membrane filter and drying it. The porous matrix containing the impregnated tetrazolium salt is laminated on the buffer-containing layer. Solvents in which a specific tetrazolium salt can be dissolved are well known. To improve the solubility of the tetrazolium salt in the solvent, a surfactant may be added to the solvent.

The thickness of each of the buffer-containing layer and the tetrazolium salt-containing layer is not critical. Preferably, the buffer-containing layer has a wet thickness of 250 μm or less, e.g., about 200 μm, and the tetrazolium salt-containing layer has a thickness of 300 μm or less, e.g., about 250 μm.

Each of the buffer-containing layer and the tetrazolium salt-containing layer is cut to a suitable size, for example, 5 mm×7 mm, fixed to a base film with a double coated tape or an adhesive, and used in the assay.

The assay of fructosamine is carried out by placing a drop of a sample on the multilayer analytical element of the present invention and measuring the developed color by a conventional method. A specific assay manner will be explained in the below described Examples.

PREFERRED EMBODIMENTS OF THE INVENTION

The present invention will be illustrated by the following Examples.

EXAMPLE 1

A buffer-containing layer was formed by mixing the following components, applying the resulting mixture on an opaque polyethylene terephthalate (PET) film at a wet thickness of 200 μm and drying it at 40° C. for 30 minutes:

| | |
|---|---|
| Sodium carbonate | 3.18 g |
| Sodium hydrogencarbonate | 0.84 g |
| Purified water | 86 g |
| PVP K-90 | 10 g |

The PET film carrying the coated buffer-containing layer was cut to a size of 5 mm×7 mm.

A tetrazolium salt-containing layer was formed by mixing the following components, impregnating a cotton or polyester fabric with the resulting mixture, and drying it at 40° C. for 30 minutes:

| | |
|---|---|
| NTB | 700 mg |
| Methanol | 10 g |
| Purified water | 14.3 g |

The tetrazolium salt-containing layer was cut to a size of 5 mm×10 mm.

Figure 1B:
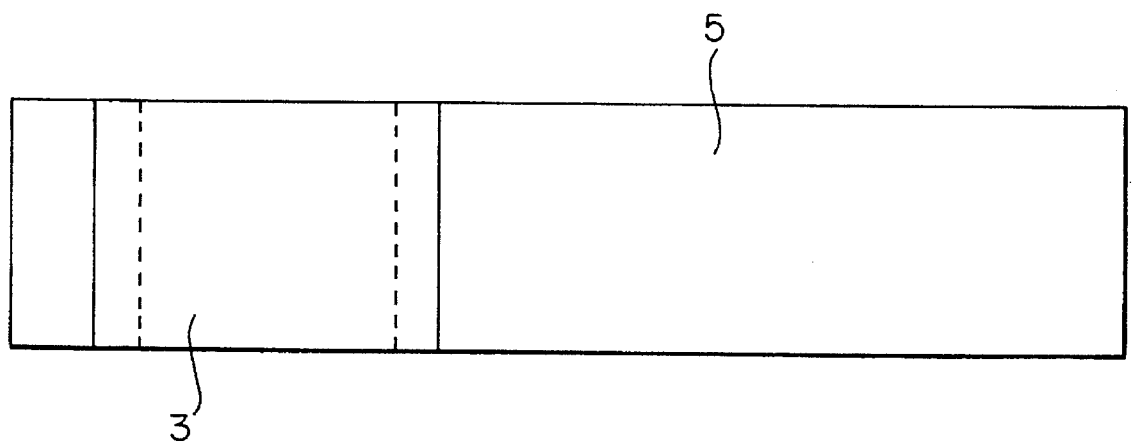

As shown in FIGS. 1A and 1B, on a base film 5 made of a PET film, the buffer-containing layer 2 carried on the PET film 1 was adhered using a double coated tape 4 (5 mm×10 mm). Since the adhesive tape was 3 mm longer than the buffer-containing layer, there remained a marginal area of 1.5 mm of the adhesive tape on each side of the buffer-containing layer.

When the tetrazolium salt-containing layer 3 (5 mm ×10 mm) was laminated on the buffer-containing layer, the former was fixed on the base film 5 by the marginal areas of the adhesive tape.

Since each layer was separately formed and laminated, the layers were separated by an air layer therebetween.

EXAMPLE 2

Figure 2A:
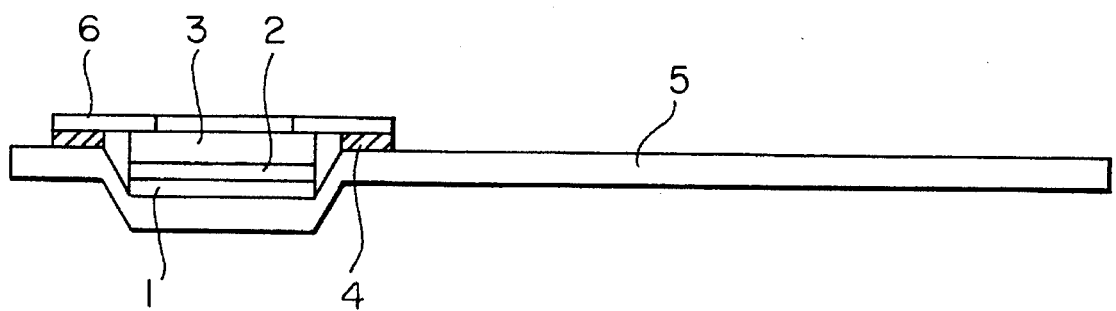
Figure 2B:
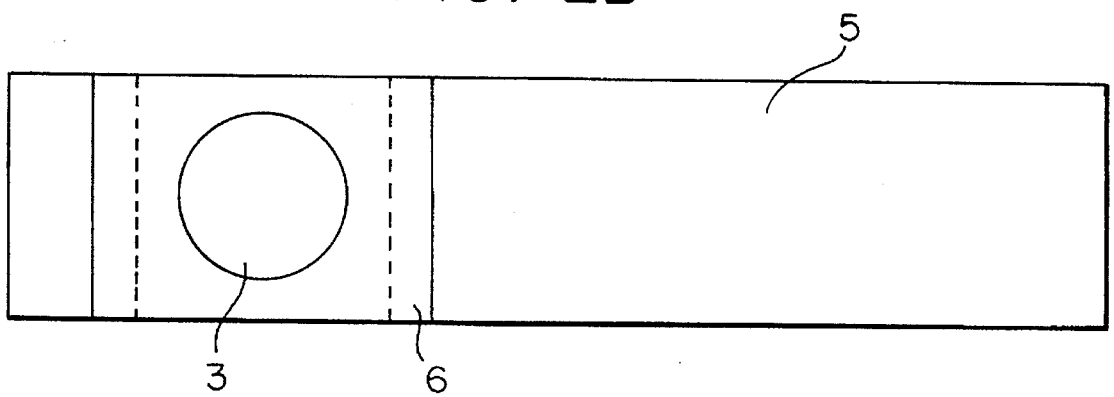

The same buffer-containing layer 2 as prepared in Example 1 and the same tetrazolium salt-containing layer 3 as prepared in Example 1, except that the size was 5 mm×7 mm were placed in a depressed area of the base film 5 shown in FIG. 2. Then, the buffer-containing layer 2 and the tetrazolium salt-containing layer 3 placed in the depressed area were mounted with a covering film 6 having a hole. The covering film 6 was adhered to the base film 5 with pieces of double coated tape 4 at both ends.

COMPARATIVE EXAMPLE

A tetrazolium salt-containing layer was formed by mixing the following components, impregnating a cotton or polyester fabric with the resulting mixture, and drying it at 40° C. for 30 minutes:

| | |
|---|---|
| NTB | 700 mg |
| Methanol | 10 g |
| Purified water | 14.3 g |

A buffer-containing layer was formed by mixing the following components, and applying the resulting mixture on an opaque PET film at a wet thickness of 200 μm:

| | |
|---|---|
| Sodium carbonate | 3.18 g |
| Sodium hydrogencarbonate | 0.84 g |
| Purified water | 86 g |
| PVP K-90 | 10 g |

Figure 3A:
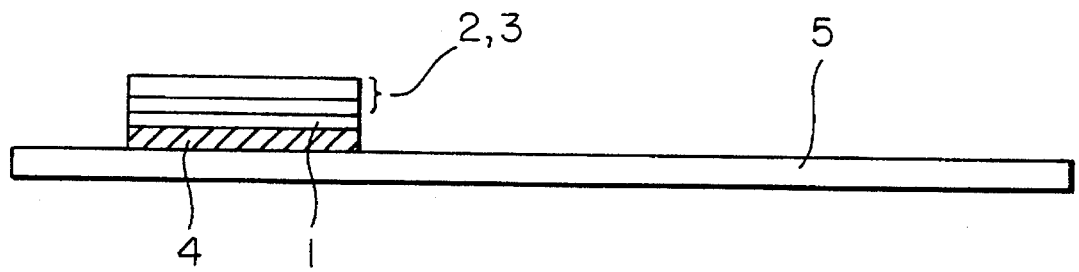
Figure 3B:
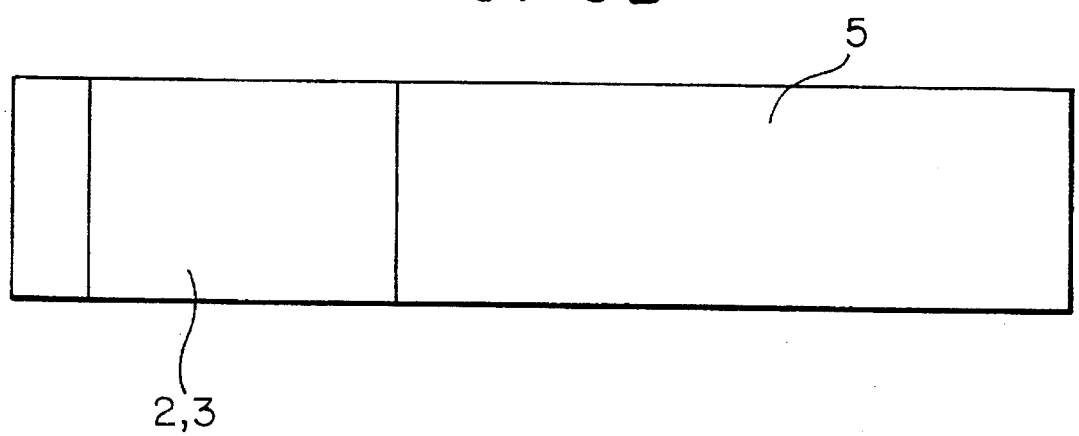

While the buffer-containing layer was still wet and soft, the above prepared tetrazolium salt-containing layer was laminated and dried at 40° C. for 30 minutes. Then, the integrated sample was cut to the size of 5 mm×7 mm and adhered using the double coated tape 4 to the base film to obtain the analytical element shown in FIGS. 3A and 3B.

EXAMPLE 3

In the same manner as in Example 1 except that a buffer-containing layer containing uricase was formed by mixing the following components, applying the resulting mixture on an opaque PET film at a wet thickness of 200 μm and drying it at 40° C. for 30 minutes:

| Sodium carbonate | 0.318 g |
| --- | --- |
| Sodium hydrogencarbonate | 0.084 g |
| Purified water | 8.6 g |
| PVP K-90 | 1.0 g |
| Uricase | 4000 units | the analytical element was produced.

The analytical elements produced in Examples 1 and 3 and Comparative Example were stored in a bottle containing a desiccant and kept in an incubator at 50° C. for 0 days, 15 days, 30 days or 60 days. Then, the reflectance on the surface of the tetrazolium salt-containing layer was measured at a wavelength of 550 nm.

As test samples, (1) purified water, (2) human serum 1 containing 210 μmol/l of fructosamine, (3) human serum 2 containing 453 μmol/l of fructosamine, and (4) human serum 3 containing 210 μmol/l of fructosamine and 10 mg/dl of uric acid were used.

Each 6 μl of the test sample were spotted on each of the analytical elements and incubated at 37° C. Then, the reflectance from 5 to 7 minutes from the start of incubation was monitored. The measured reflectance was converted to a K/S value according to the Kubelka-Munk equation, and its difference (ΔK/S) between 5 minutes and 7 minutes was calculated. The results are shown in the Table.

TABLE

| | | After keeping in an incubator for | | | |
| --- | --- | --- | --- | --- | --- |
| Example No. | Test sample | 0 day | 15 days | 30 days | 60 days |
| 1 | (Reflectance) | 92% | 91% | 89% | 87% |
| | Water | 0.002 | 0.002 | 0.003 | 0.002 |
| | Serum 1 | 0.103 | 0.104 | 0.104 | 0.104 |
| | Serum 2 | 0.208 | 0.207 | 0.209 | 0.209 |
| | Serum 3 | 0.108 | 0.109 | 0.111 | 0.110 |
| 3 | (Reflectance) | 90% | 90% | 88% | 86% |
| | Water | 0.003 | 0.003 | 0.003 | 0.004 |
| | Serum 1 | 0.101 | 0.102 | 0.103 | 0.103 |
| | Serum 2 | 0.208 | 0.208 | 0.210 | 0.210 |
| | Serum 3 | 0.103 | 0.105 | 0.105 | 0.105 |
| Comp. | (Reflectance) | 72% | 64% | 58% | 49% |
| | Water | 0.009 | 0.012 | 0.013 | 0.015 |
| | Serum 1 | 0.115 | 0.118 | 0.118 | 0.123 |
| | Serum 2 | 0.232 | 0.223 | 0.215 | 0.211 |
| | Serum 3 | 0.240 | 0.238 | 0.241 | 0.240 |

As seen from the results in the Table, in the analytical elements of Examples 1 and 3, slight coloring was observed but was hardly identified with the naked eyes. When they were stored at 50° C., there was no influence on the measured values with the serums.

In the analytical element of the Comparative Example, the reagents were mixed so that the reagent layer was colored (after 0 day) and the degree of coloring increased with time. In addition, the ΔK/S values fluctuated. These results indicate the poor reliability of the analytical element of the Comparative Example.

Since the analytical element of Example 3 contained uricase in the buffer-containing layer, the increase of Δ K/S was suppressed when uric acid was added to the serum sample.

What is claimed is:

1. A multilayer analytical element for assaying fructosamine, consisting essentially of a liquid-impermeable support, a dried buffer-containing layer which contains a buffer having a pH of 8 to 12 formed on said support, and a tetrazolium salt-containing layer which is independently prepared, dried, and laminated on said buffer-containing layer.

2. The multilayer analytical element according to claim 1, wherein said tetrazolium salt contained in said tetrazolium salt-containing layer is at least one compound selected from the group consisting of 3,3'-[3,3'-dimethoxy-(1,1'-biphenyl) -4,4'-diyl]-bis[2-(p-nitrophenyl)-5-phenyl-2H-tetrazolium chloride], 3,3'-[3,3'-dimethoxy-(1,1'-biphenyl)-4,4'-diyl]-bis [2,5-bis(p-nitrophenyl)-2H-tetrazolium chloride], 3,3'-(1,1'-biphneyl-4,4'-diyl)-bis(2,5-diphenyl-2H-tetrazolium chloride], 3-(p-iodophenyl)-2-(p-nitrophenyl)-5-phenyl-2H-tetrazolium chloride, 3-(4,5-dimethyl-2-thiazolyl)-2,5-diphenyl-2H-tetrazolium bromide and 2,5-diphenyl-3-(1-naphthyl)-2H-tetrazolium chloride.

3. The multilayer analytical element according to claim 1, wherein said buffer has a pH of 8.5 to 10.5.

4. The multilayer analytical element according to claim 1, wherein said liquid-impermeable support is a material selected from the group consisting of a plastic film, paper, and a metal foil.

5. The multilayer analytical element according to claim 1, wherein said liquid-impermeable support is a plastic film.

6. The multilayer analytical element according to claim 1, wherein said buffer is a carbonate buffer.

7. The multilayer analytical element according to claim 1, wherein said buffer-containing layer further comprises a binder.

8. The multilayer analytical element according to claim 7, wherein said binder is a hydrophilic polymer.

9. The multilayer analytical element according to claim 8, wherein said hydrophilic polymer is a member selected from the group consisting of polyvinylpyrrolidone, hydroxypropylcellulose, methylcellulose, polyacrylamide, and gelatin.

10. The multilayer analytical element according to claim 1, wherein said tetrazolium salt-containing layer is formed by impregnating a solution of said salt in a porous matrix.

11. The multilayer analytical element according to claim 10, wherein said porous matrix is a member selected from the group consisting of a filter paper, a woven fabric, a knit fabric, and a membrane filter.

12. The multilayer analytical element according to claim 1, wherein said buffer-containing layer has a wet thickness of 250 μm or less and said tetrazolium salt-containing layer has a thickness of 300 μm or less.

13. The multilayer analytical element according to claim 1, wherein said buffer-containing layer further contains uricase.

14. The multilayer analytical element according to claim 1, which is fixed on a base film using a mount or an adhesive tape.

15. The multilayer analytical element according to claim 12, wherein said buffer-containing layer has a wet thickness of about 200 μm, and said tetrazolium salt-containing layer has a thickness of about 250 μm.

16. A multilayer analytical element for assaying fructosamine, consisting essentially of a liquid-impermeable support, a dried buffer-containing layer which contains a binder, uricase, and a buffer having a pH of 8 to 12 formed on said support, and a tetrazolium salt-containing layer which is independently prepared, dried, and laminated on said buffer-containing layer.

* * * * *